United States Patent [19]

Diamond

[11] 4,166,133

[45] Aug. 28, 1979

[54] ETHYNYLBENZENE COMPOUNDS AND DERIVATIVES THEREOF TO TREAT PAIN, FEVER AND INFLAMMATION

[75] Inventor: Julius Diamond, Morris Plains, N.J.

[73] Assignee: William H. Rorer, Inc., Fort Washington, Pa.

[21] Appl. No.: 858,006

[22] Filed: Dec. 6, 1977

Related U.S. Application Data

[60] Division of Ser. No. 574,837, May 14, 1975, which is a continuation of Ser. No. 431,254, Jan. 7, 1974, Pat. No. 3,923,910, which is a division of Ser. No. 268,419, Jul. 3, 1972, Pat. No. 3,852,364.

[51] Int. Cl.² .................. A61K 31/05; A61K 31/22

[52] U.S. Cl. .................................. 424/346; 424/311
[58] Field of Search .................................. 424/346

[56] References Cited

U.S. PATENT DOCUMENTS

| 3,852,364 | 12/1974 | Diamond | 424/346 |
| 3,968,251 | 7/1976 | Lacefield et al. | 424/340 |

*Primary Examiner*—Stanley J. Friedman
*Attorney, Agent, or Firm*—Miller & Prestia

[57] ABSTRACT

A method of treating patients by administering an effective amount of a hydroxy or lower acyloxy substituted ethynylbenzene compound, and the pharmaceutical preparation thereof.

10 Claims, No Drawings

ETHYNYLBENZENE COMPOUNDS AND DERIVATIVES THEREOF TO TREAT PAIN, FEVER AND INFLAMMATION

This is a division of application Ser. No. 574,837, filed May 14, 1975. Application Ser. No. 574,837 is a continuation of application Ser. No. 431,254, filed Jan. 7, 1974, now U.S. Pat. No. 3,923,910, which is a division of application Ser. No. 268,419, filed July 3, 1972, now Patent No. 3,852,364.

SUMMARY OF THE INVENTION

This invention describes novel ethynylbenzene compounds and derivatives and their use in therapeutic compositions. In addition, this invention describes the preparation of these ethynylbenzene compounds and their derivatives. When the compounds of this invention are administered to mammals, they afford significant treatment for the relief of inflammation and associated pain and fever.

They further provide analgesic and antipyretic methods for the relief and treatment of pain and fever.

BACKGROUND OF THE INVENTION

Continued studies have been carried out during the last decade to develop drugs which would significantly inhibit the development of inflammation and relieve pain and fever as well as the pain and fever associated with inflammation. While much of this effort has been carried out in the steroid field, there have been compounds developed which are non-steroidal but all of this type are acidic in nature, e.g., arylalkanoic acids, heterylalkanoic acids, pyrazolidinediones. While many of these compounds have been found to be effective, they have had the drawback of causing various side effects, in particular, gastric hemorrhage and ulceration.

I have unexpectedly found that ethynylbenzene compounds have pharmacological properties which are useful for the relief and inhibition of inflammation conditions and are neutral substances.

I have also found that the compounds of this invention are effective in the treatment of inflammation and the control of arthritic conditions associated with inflammation, without producing gastric hemorrhage or ulceration commonly associated with anti-inflammatory agents.

I have further found that the ethynylbenzene compounds and derivatives of this invention are novel.

I have also found that the compounds of this invention possess useful, analgesic and antipyretic properties and are useful in the treatment of pain and fever.

I have still further found an entirely new class of antiinflammatory, analgesic and antipyretic pharmaceutical compositions which contain an ethynylbenzene compound derivative thereof as active ingredient.

I have also found a convenient method for synthesizing these compounds.

DESCRIPTION AND PREFERRED EMBODIMENTS

This invention comprises a class of novel chemical compounds which are ethynylbenzene compounds or derivatives. Also the benzene ring is further substituted.

This invention also describes a new method for treating inflammation as well as pain and fever and also novel therapeutic compositions.

The compounds of this invention can be represented by the generic structure which is described by the general formula I;

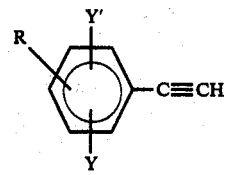

where
R is alkyl, cycloalkyl, alkylcycloalkyl, cycloalkenyl, aryl or substituted aryl where the substituent is Y';

Y, Y' and Y" are hydrogen, alkyl, halo, nitro, amino, acylamino, mono and diloweralkylamino, mercapto, acylthio, loweralkylthio, loweralkylsulfinyl, loweralkylsulfonyl, hydroxy, loweralkoxy, acyloxy, haloloweralkyl, cyano or acetyl;

with the proviso that when R is phenyl then at least one of Y and Y' are other than hydrogen.

The para position is the preferred position for the R substituents.

The meta position is the preferred position for the Y and Y' substituents, and the ortho position is the preferred position for the Y" substituents.

More specifically, the chemical compounds of this invention which have particular usefulness as antiinflammatory, analgesic and antipyretic agents and whose properties are preferred are described by formulae II–IV:

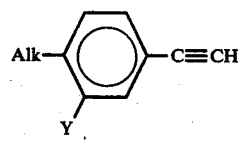

where Alk is alkyl having 3–7 carbon atoms.

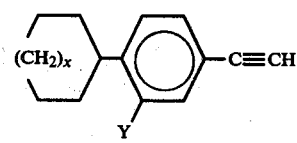

where x is 0–2.

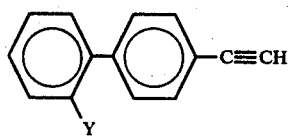

Those compounds whose properties are even more preferred are described by formulae II–III
where
Y is hydrogen, halo, nitro, cyano, loweralkylsulfonyl or haloloweralkyl; and
x=1.

The more preferred compounds of formula IV are those where Y is halo.

Compounds which are most preferred are those where Y is halo and chloro is particularly preferred.

In the descriptive portions of this invention the following definitions apply:

"Alkyl" refers to a loweralkyl hydrocarbon group containing from 1 to about 7 carbon atoms which may be straight chained or branched.

"Alkenyl" refers to an unsaturated or partially unsaturated hydrocarbon group containing from 2 to about 7 carbon atoms which may be straight chained or branched.

"Cycloalkyl" refers to a hydrocarbon ring having up to about seven carbon atoms.

"Cycloalkenyl" refers to a partially unsaturated hydrocarbon ring having up to about seven carbon atoms.

"Aryl" refers to any benzenoid or non-benzenoid aromatic group but preferably phenyl.

"Alkoxy" refers to a loweralkoxy group containing from 1 to about 6 carbon atoms which may be straight chained or branched.

"Acyl" refers to any organic radical derived from an organic acid by the removal of its hydroxyl group such as formyl, acetyl, propionyl.

It should also be realized by one skilled in the art that the following compounds may also be employed in the practice of this invention where R is aryloxy, arylthio, arylamino, aroyl or heteryl.

The preferred "aroyl" is benzoyl, loweralkylbenzoyl such as toluoyl or halobenzoyl such as p-chlorobenzoyl, etc.

"Heteryl" refers to a heterocyclic ring having 5-7 atoms which is saturated, partially saturated or unsaturated and containing one or more of the same or different hetero atoms of N, S or O.

Representative heteryl rings include such as thienyl, furyl, pyridyl, pyrazinyl, pyrimidinyl, pyridazinyl, triazinyl, isoxazolyl, isothiazolyl, pyrrolyl, imidazolyl, pyrazolyl, pyranyl, 2H-pyrrolyl, imidazolidinyl, imidazolinyl, pyrazolidinyl, pyrrolidinyl, pyrrolinyl, piperidyl, piperazinyl, morpholinyl.

The compounds of this invention may be prepared by the following general procedures.

Condensation of a substituted benzene compound with a loweralkyl or aralkyl oxalyl chloride in the presence of anhydrous aluminum chloride results in a p-substitutedphenylglyxoylate. The loweralkyl or aralkyl esters of the p-substitutedphenyl glyoxylic acid may be halogenated or nitrated to obtain the corresponding loweralkyl esters of a 3-halo-4-substitutedphenylglyoxylic acid or a 3-nitro-4-substitutedphenylglyoxylic acid. Chlorination or bromination may be carried out in the presence of a small amount of iodine dissolved in an inert solvent such as carbon tetrachloride. A solution of chlorine or bromine is then added while the temperature is held near 0° C. Nitration is carried out with fuming nitric acid at about 0° C. The following reaction equations illustrate this method.

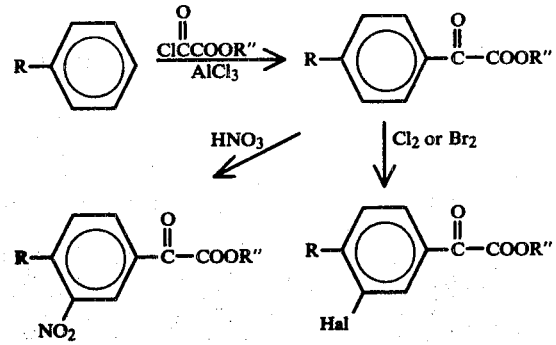

where R is as described above and Hal is chloro.

Appropriately desired end products having various Y and Y' substitutents can be prepared by using suitable reactions in order to convert one group to another. Thus, for example, a 3-halo-4-substitutedphenylglyoxylate in which halo is chloro, bromo or iodo may be (a) reacted with cuprous cyanide in quinoline at about 150° C. to produce a 3-cyano-4-substitutedphenylglyoxylate;

(b) reacted with trifluoromethyliodide and copper powder at about 150° C. in dimethylformamide to obtain a 3-trifluoromethyl-4-substitutedphenylglyoxylate: [as described in *Tetrahedron Letters*: 47,4095 (1959)];

(c) reacted with cuprous methanesulfinate in quinoline at about 150° C. to obtain a 3-methylsulfonyl-4-substitutedphenylglyoxylate.

A 3-nitro-4-substitutedphenylglyoxylate may be selectively hydrogenated to the corresponding amine.

A 3-amino-4-substitutedphenylglyoxylate may then be (a) mono- or dialkylated with loweralkyl halides or sulfates or acylated with loweracyl chlorides or anhydrides;

(b) diazotized to the diazonium fluoroborate which is then thermally decomposed to the 3-fluoro-4-substitutedphenylglyoxylate, (c) diazotized and heated in an aqueous medium to form the 3-hydroxy-4-substitutedphenylglyoxylate or heated in an alcohol to form the 3-alkoxy-4-substitutedphenylglyoxylate. The hydroxyl group may also be alkylated with loweralkyl halides or sulfates to the alkoxyl group or acylated with loweracyl chlorides or anhydrides to the acyloxy compound in the presence of a tertiary amine such as pyridine, (d) diazotized followed by a Sandmeyer type reaction to yield the halo group, (e) diazotized and heated with an aqueous solution of potassium iodide to prepare the 3-iodo-4-substitutedphenylglyoxylate, (f) diazotized and followed by addition of cuprous cyanide to obtain the 3-cyano-4-substitutedphenylglyoxylate which in turn may be esterified with an alcohol or hydrolyzed to the amide or carboxylic acid of the glyoxylic acid, (g) diazotized followed by reaction with potassium ethylxanthate followed by hydrolysis to obtain 3-mercapto-4-substitutedphenylglyoxylic acid which can be esterified to a 3-mercapto-4-substitutedphenylglyoxylate. This in turn can be lower alkylated to the lower alkylthio and oxidized to the loweralkylsulfinyl and loweralkylsulfonyl groups or acylated to the acylthio compounds.

A second nitration or halogenation may be carried out on the 3-substitutedglyoxylate to obtain the corresponding 3,5-disubstitutedglyoxylate. This may be carried out at any appropriate stage of the synthesis in order to obtain the desired substituents. Thus, for example, a 3-chloro-4-substitutedphenylglyoxylate may be nitrated as above to obtain a 3-chloro-5-nitro-4-substitutedphenylglyoxylate or chlorinated to obtain a 3,5-dichloro-4-substitutedphenylglyoxylate. A 3-nitro-4-substitutedphenylglyoxylate can be nitrated to give a 3,5-dinitro-4-substitutedphenylglyoxylate.

Reduction of the glyoxylate ester is accomplished by lithium aluminum hydride to give the 1,2-ethanediol (a). When the 1,2-ethanediol is treated with periodic acid the corresponding aldehyde is prepared (b). Alternatively, the glyoxylate ester may be converted to the glyoxylic acid by acid hydrolysis, and the latter with heat decarboxylated to the substituted benzaldehyde. The latter method is used when Y or Y' are substituents sensitive to LiAlH$_4$ reduction, e.g., NO$_2$, SH, SR, SOR, I.

Claisen condensation of a substitutedbenzaldehyde with an acetic acid ester (preferably a loweralkyl or benzyl ester) in the presence of a metal alkoxide results is a β-substitutedphenylacrylic ester. The aldehyde may also be subjected to a Perkin reaction with acetic anhydride and an acetic acid salt or through a Knoevenogel condensation using malonic acid and ammonia in an amine base to obtain β-substitutedphenylacylic acid (c). Addition to the double bond with halogen (preferably bromine) results in an α,β-dibromopropionic acid or ester (d). When the α,β-dibromopropionate is added to an alcoholic potassium hydroxide solution and heated for several hours the corresponding propiolic acid is prepared (e). Heating the propiolic acid at raised temperature in quinoline for 2–10 hours results in the desired acetylene compound (f).

where R, Y and Y' are as described above and R" is loweralkyl or butyl.

When Y and Y' substitution is desired in the ortho position of the phenyl ring then the halogenation and nitration may be carried out in a similar manner but on the propiolic acid or ester or on the desired acetylene.

A further preparation of the compounds of this invention may be carried out starting with a substitutedacetophenone and reacting the keto function with a halogenating agent such as phosphorus pentachloride and phosphorus oxychloride and the like. The resultant dihalo compound is then dehalogenated using sodamide in liquid ammonia to obtain the desired acetylene. This is particularly useful in obtaining the 3-halo-4-substitutedphenylacetylene from 3-halo-4-substitutedacetophenone.

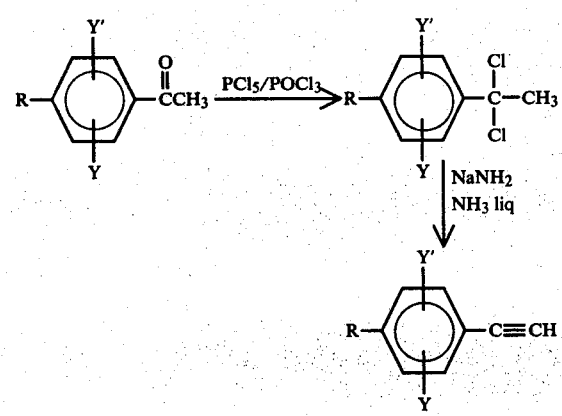

I have found that the compounds of this invention exercise a useful degree of anti-inflammatory activity in mammals and are effective in the treatment of associ-

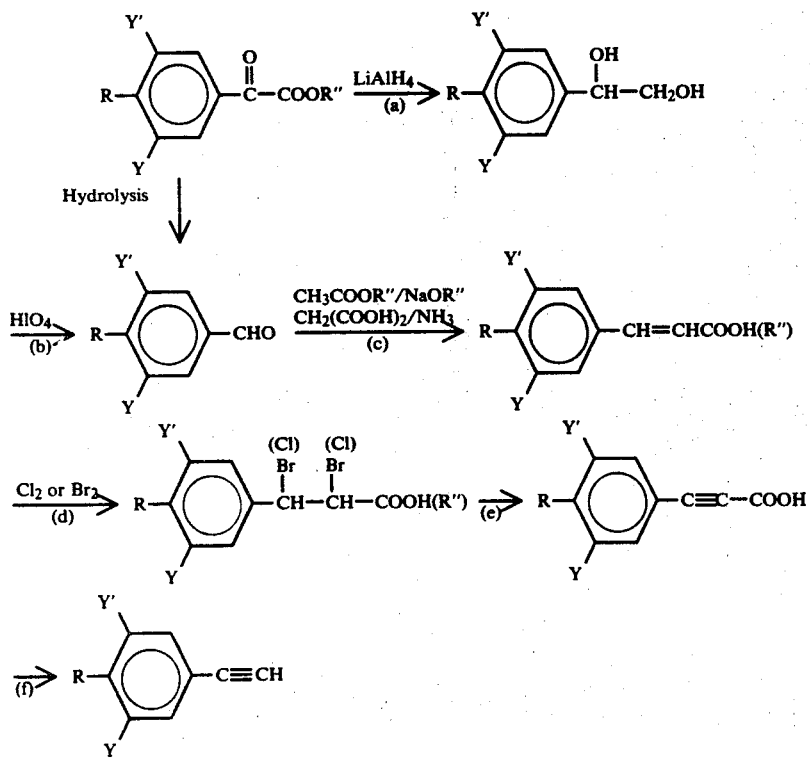

ated pain and fever and in like conditions which are responsive to treatment with anti-inflammatory agents. In general, the compounds of this invention are indicated for a wide variety of mammalian conditions where the symptoms of inflammation and associated fever and pain are manifested. Exemplary of such conditions are: rheumatic diseases such as rheumatoid arthritis, osteoarthritis and other degenerative joint diseases; soft-tissue rheumatism such as tendinitis; muscular rheumatism such as sciatica; pain and inflammation associated with dental surgery and similar human and veterinary disease conditions exhibiting the foregoing symptoms requiring the use of an anti-inflammatory, analgesic and/or antipyretic agent.

I have also found that the compounds of this invention show a marked degree of analgesic activity and are effective in the relief of pain and fever. These compounds are essentially devoid of gastric hemorrhage side effects.

For all the above purposes, the compounds of this invention are normally administered orally, topically, parenterally or rectally. Orally, these may be administered in tablets, capsules, suspensions or syrups; the optimum dosage, of course, depending on the particular compound being used and the type and severity of the condition being treated. In any specific case the appropriate dosage selected will further depend on factors of the patient which may influence response to the drug; for example, general health, age, weight, etc. Although the optimum quantities of the compounds of this invention to be used in such manner will depend on the compound employed and the particular type of disease condition treated, oral dose levels of preferred compounds when administered to a mammal in dosages of 0.5 to 100 milligrams per kilogram of body weight per day are particularly useful. The preferred range is 0.5 to 15 mg/kg. Comparative dosages may be used in topical, parenteral or rectal administration.

Dosage forms may be prepared according to any method known to the art for the manufacture of pharmaceutical compositions and such compositions may contain one or more agents; for example, sweetening agents, flavoring agents, coloring agents, preserving agents, etc. Further, the active acetylenic compounds may be administered alone or in admixture with antacids such as sodium bicarbonate, magnesium carbonate, magnesium hydroxide, aluminum hydroxide, magnesium silicate, etcl, and non-toxic pharmaceutically acceptable excipients. Such excipients may be, for example, inert diluents such as calcium carbonate, lactose, etc., granulating and disintegrating agents; for example maize starch, alginic acid, etc., lubricating agents; for example, magnesium stearate, talc, etc., binding agents; for example, starch gelatin, etc., suspending agents; for example, methylcellulose, vegetable oil, etc., dispersing agents; for example, lecithin, etc., thickening agents; for example, beeswax, hard paraffin, etc., emulsifying agents; for example, naturally-occurring gums, etc., and non-irritating excipients; for example, cocoa butter and polyethylene glycols.

Various tests in animals can be carried out to show the ability of the acetylenic compounds of this invention to exhibit reactions that can be correlated with anti-inflammatory activity in humans. One such test is the carrageenan paw edema test, which shows the ability of the instant compounds to inhibit edema induced by injection of an inflammatory agent such as carrageenan into the tissues of the paw of a rat against non-inflammed controls. This carrageenan testing method is known to correlate well with anti-inflammatory activity in humans and is a standard test used to determine anti-inflammatory activity. This correlation can be shown by the activities of compounds known to be clinically active including such as aspirin, phenylbutazone, cortisone, hydrocortisone, indomethacin and prednisolone. In view of the results of this test, the acetylenic compounds of this invention can be considered to be active anti-inflammatory agents.

A further test to show anti-inflammatory activity is the polyarthritis test in rats. This test is carried out on the animal model which closely resembles human arthritis and is widely used in the art. This is outlined by Winter & Nuss in *Arthritis and Rheumatism* 9: 394, (1966). In view of the results of this test, the acetylenic compounds of this invention can be considered to be active anti-inflammatory agents.

One method for measuring analgesic activity is the acetic acid writhing test as outlined by Siegmund et al in the *Proc. Soc. Exp. Biol. Med.* 95: 729-731, (1957). This method involves the intraperitoneal injection of 60 mg/kg of HOAc (0.6% solution; 0.1 ml/10 g) into male albino mice which produces a syndrone characterized by stretching movement. Analgesics prevent or suppress the stretch.

In view of the results of this test, the acetylenic compounds of this invention are considered to demonstrate non-narcotic analgesic activity.

One method of measuring gastric hemorrhage is as follows.

Albino male rats weighing 100-120 g are fasted for 24 hours but given free access to water. The animals are placed in groups of 10 animals per dose and dosed by gastric gavage at a volume of 1 ml/100 g body weight with test compound suspended in 0.5% methylcellulose. A control group receives only 0.5% methylcellulose. Four hours after administration of compound, the animals are sacrificed and the rumens of the stomachs assayed for gastric hemorrhage. Hemorrhage is defined as an area of blood which is 1 mm or larger at the largest diameter. Diameter of the hemorrhage is recorded. The number of animals in each group with stomachs having at least one area of hemorrhage is recorded. The presence of areas of blood smaller than 1 mm, defined as petechiae, is noted but not counted in the assay. The percent hemorrhage for each group is statistically analyzed to determine the dose magnitude ($ED_{50}$) which causes production of gastric hemorrhage in 50% of the animals.

The following are detailed examples which show the preparation of the compounds of this invention. They are to be construed as illustrations of said compounds and are not intended to be limitations thereof.

EXAMPLE 1

Ethyl 4-cyclohexylphenylglyoxylate

Cyclohexylbenzene 53 g. (0.33 mole) and 50.5 g. (0.37 mole) of ethyl oxalyl chloride are dissolved in 200 ml. of dry 1,1,2,2-tetrachloroethane. Anhydrous aluminum chloride 52 g. (0.39 mole) is added in small portions to the reaction mixture with stirring over 2 hours. During the addition, the temperature of the mixture is maintained between 16°-18° C. The mixture is stirred for an additional hour and allowed to stand overnight. The solution is then slowly poured into 1500 ml. of iced saline solution with stirring. After standing, two layers form. The aqueous layer is extracted with 500 ml. of ether and the ether extract is combined with the organic layer which is dissolved in 1500 ml. of ether and separated. The ether solution is washed with 10×100 ml. portions of a 1:1 mixture of saturated sodium chloride solution and 10% HCl solution, and 5×100 ml. portions of water. The ether solution is then dried over anhydrous magnesium sulfate for 1 hour and filtered. The solvents are removed by distillation under reduced pressure and the residue distilled to obtain ethyl 4-cyclohexylphenylglyoxylate.

When cyclohexylbenzene in the above example is replaced with cyclopentylbenzene, cycloheptylbenzene, 2'-methylcyclohexylbenzene, biphenyl, i-propylbenzene, i-butylbenzene, t-butylbenzene, cyclohex-1-enylbenzene, cyclohex-3-enylbenzene then the products prepared are ethyl p-cyclopentylphenylglyoxylate, ethyl p-cycloheptylphenylglyoxylate, ethyl p-(2'-methylcyclohexyl)phenylglyoxylate, ethyl p-biphenylylglyoxylate, ethyl p-i-propylphenylglyoxylate, ethyl p-i-butylphenylglyoxylate, ethyl p-t-butylphenylglyoxylate.

EXAMPLE 2

Ethyl 3-chloro-4-cyclohexylphenylglyoxylate

Ethyl p-cyclohexylphenylglyoxylate 98.9 g. (0.38 mole) and 6.1 g. of iodine (0.048 mole) and dissolved in 100 ml. of carbon tetrachloride. To this solution is added a solution of 40.4 g. (0.57 mole) of chlorine dissolved in 365 ml. of carbon tetrachloride over a period of 2 hours. During the addition, the temperature of the reaction mixture is maintained at 0° C. The mixture is stirred for 3 hours and allowed to stand with gradual warming to room temperature over 15 hours. The solvent is removed by distillation under reduced pressure. The residue is fractionally distilled to obtain ethyl 3-chloro-4-cyclohexylphenylglyoxylate.

When ethyl p-cyclohexylphenylglyoxylate in the above example is replaced with the esters of Example 1 then the corresponding product of Table I below is prepared.

TABLE I ethyl 3-chloro-4-cyclopentylphenylglyoxylate
ethyl 3-chloro-4-cycloheptylphenylglyoxylate
ethyl 3-chloro-4-(2'-methylcyclohexyl)phenylglyoxylate
ethyl 3-chloro-4-biphenylylglyoxylate
ethyl 3-chloro-4-i-propylphenylglyoxylate
ethyl 3-chloro-4-i-butylphenylglyoxylate
ethyl 3-chloro-4-t-butylphenylglyoxylate

EXAMPLE 3

Ethyl 3,5-dichloro-4-cyclohexylphenylglyoxylate

Ethyl p-cyclohexylphenylglyoxylate, 49.5 g. (0.19 mole) and 6.1 g. of iodine are dissolved in 100 ml. of carbon tetrachloride. To this solution is added a solution of 56.7 g. (0.8 mole) of chlorine dissolved in 500 ml. of carbon tetrachloride over a period of 3 hours. During the addition, the temperature of the reaction mixture is maintained at 0° C. The mixture is stirred for 3 hours and allowed to stand with gradual warming to room temperature over 30 hours. The solvent is removed in vacuo. The residue is fractionally distilled to obtain ethyl 3,5-dichloro-4-cyclohexylphenylglyoxylate.

When ethyl p-cyclohexylphenylglyoxylate in the above example is replaced by the esters of Example 1, then the corresponding product is prepared.

EXAMPLE 4

When bromine is used in place of chlorine in Example 2, the products obtained are shown in Table I below.

TABLE I ethyl 3-bromo-4-cyclopentylphenylglyoxylate
ethyl 3-bromo-4-cycloheptylphenylglyoxylate
ethyl 3-bromo-4-cyclohexylphenylglyoxylate
ethyl 3-bromo-4-(2'-methylcyclohexyl)phenylglyoxylate
ethyl 3-bromo-4-biphenylylglyoxylate
ethyl 3-bromo-4-i-propylphenylglyoxylate
ethyl 3-bromo-4-i-butylphenylglyoxylate
ethyl 3-bromo-4-t-butylphenylglyoxylate When bromine is used in place of chlorine in Example 3, the corresponding products are obtained.

EXAMPLE 5

Ethyl 3-nitro-4-cyclohexylphenylglyoxylate

Ethyl p-cyclohexylphenylglyoxylate 17.2 g. (0.066 mole) is added to ice-cold concentrated sulfuric acid (18 ml) and stirred with cooling for 5 minutes. Concentrated nitric acid (Sp. G. 1.51) (2.5 ml.) is added dropwise, maintaining the temperature between 30° and 40° by water cooling if necessary. After addition of the nitric acid is complete, the mixture is stirred for ½ hour, then poured into water. The mixture is made alkaline with sodium hydroxide, then extracted with ether. The ether extract is washed, dried over sodium sulfate, evaporated and the residue is fractionally distilled to obtain ethyl 3-nitro-4-cyclohexylphenylglyoxylate.

When ethyl p-cyclohexylphenylglyoxylate in the above example is replaced by the esters of Example I, then the corresponding product of Table I below is prepared.

TABLE I ethyl 3-nitro-4-cyclopentylphenylglyoxylate
ethyl 3-nitro-4-cycloheptylphenylglyoxylate
ethyl 3-nitro-4-(2'-methylcyclohexyl)phenylglyoxylate
ethyl 3-nitro-4-biphenylylglyoxylate
ethyl 3-nitro-4-i-propylphenylglyoxylate
ethyl 3-nitro-4-i-butylphenylglyoxylate
ethyl 3-nitro-4-t-butylphenylglyoxylate When ethyl p-cyclohexylphenylglyoxylate in the above example is replaced by the esters of Examples 3 and 4, then the corresponding product is prepared.

EXAMPLE 6

Ethyl 3,5-dinitro-4-cyclohexylphenylglyoxylate

Ethyl p-cyclohexylphenylglyoxylate 17.2 g. (0.066 mole) is added to ice-cold concentrated sulfuric acid (54 ml.) and stirred with cooling for 5 minutes. Concentrated nitric acid (Sp. G. 1.51) (7.5 ml.) is added dropwise, maintaining the temperature between 30° and 40° by water cooling if necessary. After addition of the nitric acid is complete, the mixture is stirred for 3 hours, then poured into water. The mixture is made alkaline with sodium hydroxide, then extracted with ether. The ether extract is washed, dried over sodium sulfite, evaporated and the residue is fractionally distilled to obtain ethyl 3,5-dinitro-4-cyclohexylphenylglyoxylate.

When ethyl p-cyclohexylphenylglyoxylate in the above example is replaced by the esters of Example 1, then the corresponding product is prepared.

EXAMPLE 7

Ethyl 3-trifluoromethyl-4-cyclohexylphenylglyoxylate

To a solution of 0.01 moles of ethyl 3-bromo-4-cyclohexylphenylglyoxylate in 50 ml. of dimethylformamide is added 0.15 moles of trifluoromethyl iodide and 0.02 g. of copper powder. The reaction is shaken in a sealed tube for 5 hours at 140° C., cooled, and then filtered and evaporated in vacuo. 200 ml. of water is added to the residue and extracted with ether. The ether extract is dried, evaporated to dryness and distilled to obtain ethyl 3-trifluoromethyl-4-cyclohexylphenylglyoxylate.

When ethyl 3-bromo-4-cyclohexylphenylglyoxylate in the above example is replaced by equimolar amounts of the appropriate compounds of Examples 4 and 5, then the corresponding product is obtained.

EXAMPLE 8

Ethyl 3-amino-4-cyclohexylphenylglyoxylate

A mixture of 15.3 g. (0.05 moles) of ethyl 3-nitro-4-cyclohexylphenylglyoxylate in 100 ml. methanol containing 0.05 mole citric acid and 1.5 g. of 5% palladium-on-carbon is shaken with hydrogen at 3 atm. pressure and 27° C. until 3 moles of hydrogen are absorbed. The mixture is filtered, washed with methanol and the filtrate concentrated in vacuo to obtain ethyl 3-amino-4-cyclohexylphenylglyoxylate, isolated as the citrate salt.

When ethyl 3-nitro-4-cyclohexylphenylglyoxylate in the above example is replaced by equimolar amounts of the appropriate compounds of Examples 5 and 6, then the corresponding products are obtained.

EXAMPLE 9

Ethyl 3-methylamino-4-cyclohexylphenylglyoxylate

To a solution of 0.01 moles of ethyl 3-amino-4-cyclohexylphenylglyoxylate in 100 ml. of pyridine is added 0.1 moles of methyl iodide. The reaction mixture is stirred overnight at room temperature, filtered and concentrated. The residue is distilled to obtain ethyl 3-methylamino-4-cyclohexylphenylglyoxylate.

When ethyl 3-amino-4-cyclohexylphenylglyoxylate in the above example is replaced by equimolar amounts of the compounds of Example 8, then the corresponding products are obtained.

When 0.01 moles of acetyl chloride is used in place of methyl iodide in the above example, then the product prepared is ethyl-3-acetylamino-4-cyclohexylphenylglyoxylate.

EXAMPLE 10

Ethyl 3-dimethylamino-4-cyclohexylphenylglyoxylate

A solution of 0.005 moles of ethyl 3-nitro-4-cyclohexylphenylglyoxylate and 1.6 ml. of 37% formaldehyde in 50 ml. of methanol is shaken with hydrogen over 0.5 g. of 5% palladium-on-charcoal at 42 lbs. and 27° C. until five moles of hydrogen are absorbed. The catalyst is filtered off and the filtrate is evaporated in vacuo. The residue is then distilled to obtain ethyl 3-dimethylamino-4-cyclohexylphenylglyoxylate.

When ethyl 3-nitro-4-cyclohexylphenylglyoxylate in the above example is replaced by equimolar amounts of the appropriate compounds of Examples 5 and 6, then the corresponding products are obtained.

EXAMPLE 11

Ethyl 3-cyano-4-cyclohexylphenylglyoxylate

To 29.4 g. (0.1 moles) of ethyl 3-amino-4-cyclohexylphenylglyoxylate in 35 ml. of 28% hydrochloric acid and 100 ml. of cracked ice to maintain the temperature at 0° C. is added a solution of 7.1 g. (0.102 moles) of sodium nitrite in 20 ml. of water. The reaction mixture is then neutralized with sodium carbonate. This diazonium mixture is added to a cuprous cyanide solution (prepared from 31.5 g. of copper sulfate and 16.2 g. of sodium cyanide in 75 ml. of water). 250 ml. of toluene is also added and the mixture is stirred for ¼ hour. The reaction is then allowed to stir an additional 2 hours while warming gradually to 50° C. This is then cooled and the toluene separated, dried over sodium sulfate and evaporated to dryness to obtain ethyl 3-cyano-4-cyclohexylphenylglyoxylate.

When ethyl 3-amino-4-cyclohexylphenylglyoxylate in the above example is replaced by equimolar amounts of the compounds of Example 8, then the corresponding products are obtained.

EXAMPLE 12

Ethyl 3-fluoro-4-cyclohexylphenylglyoxylate

To 44.2 g. (0.15 moles) of ethyl 3-amino-4-cyclohexylphenylglyoxylate is added at 0° C. 44 ml. of 1.5 moles of concentrated hydrochloric acid. The reaction mixture is maintained at 0° C. and the diazonium salt is prepared with 23.2 g. (0.32 moles) of 95% sodium nitrite in 80 ml. of water. To this mixture is rapidly added a solution of 10.4 g. (0.17 moles) of boric acid dissolved in 22 g. (0.66 moles) of 60% hydrofluoric acid. The reaction mixture is then stirred for ¼ hour and filtered, washed with 3×25 ml. of water, 2×25 ml. of methanol and 25 ml. of ether. The residual cake is then treated in vacuo. The treated cake is then placed in a distilling flask and heated to permit spontaneous decomposition. After the decomposition, the residue is then fractionally distilled to obtain ethyl 3-fluoro-4-cyclohexylphenylglyoxylate.

When ethyl 3-amino-4-cyclohexylphenylglyoxylate in the above example is replaced by the compounds of Example 8, then the corresponding products are obtained.

EXAMPLE 13

3-Hydroxy-4-cyclohexylphenylglyoxylic acid

To 4.5 g. of ethyl 3-amino-4-cyclohexylphenylglyoxylate suspension in 125 ml. of 80% hydrochloric acid and cooled to 0° C. is added dropwise a solution of 1.2 g. of sodium nitrite in 15 ml. of water. After about 10 min., 200 ml. of 50% hydrochloric acid is added portion wise and stirred for 15 hours. The reaction mixture is then poured onto ice water and extracted with chloroform, dried over sodium sulfate and concentrated in vacuo. The residue is crystallized to obtain 3-hydroxy-4-cyclohexylphenylglyoxylic acid.

The ethyl ester of the product is formed by reaction with absolute ethanol containing a small amount of anhydrous hydrochloric acid.

When ethyl 3-amino-4-cyclohexylphenylglyoxylate in the above example is replaced by equimolar amounts of the compounds of Example 8, then the corresponding products are obtained.

EXAMPLE 14

Ethyl 3-methoxy-4-cyclohexylphenylglyoxylate

To a stirred suspension of 0.01 moles of sodium hydride in 25 ml. of dry dimethylformamide which has been cooled to 0° C. is added dropwise a solution of 0.01 moles of ethyl 3-hydroxy-4-cyclohexylphenylglyoxylate in 10 ml. of dimethylformamide. The reaction mixture is stirred for 15 minutes and 0.015 moles of methyliodide is then added dropwise. The mixture is allowed to stir overnight at room temperature. 200 ml. of water is added and the resulting mixture is extracted well with ether. The ether extract is washed with water, dried over sodium sulfate, evaporated to dryness and distilled to obtain ethyl 3-methoxy-4-cyclohexylphenylglyoxylate.

When ethyl 3-hydroxy-4-cyclohexylphenylglyoxylate in the above example is replaced by equimolar amounts of the compounds of Example 13, then the corresponding products are obtained.

When 0.01 moles of acetyl chloride is used in place of methyliodide in the above reaction, then the product prepared is ethyl 3-acetyloxy-4-cyclohexylphenylglyoxylate.

EXAMPLE 15

3-Bromo-4-cyclohexylphenylglyoxylic acid

To 11.1 g. (0.044 moles) of ethyl 3-amino-4-cyclohexylphenylglyoxylate suspension in 225 ml. of 40% hydrobromic acid and cooled to 0° C. is added dropwise a solution of 2.34 g. of sodium nitrite in 30 ml. of water. To this mixture is added a solution of 20 g. of cuprous bromide in 350 ml. of 40% hydrobromic acid added portion wise and stirred for 15 hours. The reaction mixture is then poured onto ice water, extracted with chloroform, dried over sodium sulfate and concentrated in vacuo. The residue is then crystallized to obtain 3-bromo-4-cyclohexylphenylglyoxylic acid.

The ethyl ester of the product is formed by reaction with absolute ethanol containing a small amount of anhydrous hydrochloric acid.

When ethyl 3-amino-4-cyclohexylphenylglyoxylate in the above example is replaced by the compounds of Example 8, then the corresponding products are obtained.

EXAMPLE 16

3-Iodo-4-cyclohexylphenylglyoxylic acid

To 0.05 moles of ethyl 3-amino-4-cyclohexylphenylglyoxylate dissolved in a mixture of 50 g. of ice water and 0.06 moles of concentrated sulfuric acid at 0° C. is added a solution of 0.05 moles of 95% sodium nitrite in 8 ml. of water. Stirring is continued for ½ hour and then 1.5 ml. of concentrated sulfuric acid is added. This solution is poured into an ice cold solution of 0.06 moles of potassium iodide in 10 ml. of water. To this is added 0.075 g. copper bronze with stirring and the solution is warmed slowly on a water bath to about 80° C. for 2 hours. After cooling to room temperature the reaction mixture is extracted thrice with 15 ml. portions of chloroform. This is then washed with dilute thiosulfate solution, water, dried over sodium sulfate and evaporated in vacuo. The residue is crystallized to obtain 3-iodo-4-cyclohexylphenylglyoxylic acid.

The ethyl ester of the product is formed by reaction with absolute ethanol containing a small amount of anhydrous hydrochloric acid.

When ethyl 3-amino-4-cyclohexylphenylglyoxylate in the above example is replaced by equimolar amounts of the compounds of Example 8, then the corresponding products are obtained.

EXAMPLE 17

3-Mercapto-4-cyclohexylphenylglyoxylic acid

To 17.3 g. of ethyl 3-amino-4-cyclohexylphenylglyoxylate in 11.1 ml. of concentrated hydrochloric acid and 20 g. of ice is added 4.1 g. of sodium nitrite in 2 ml. of water. This mixture is stirred for 10 min. and then added gradually to an ice cold solution of 10.3 g. of potassium ethyl xanthate in 14 ml. of water. The reaction is gradually heated over 45 minutes to 50° C. and stirred an additional 45 minutes. The mixture is then cooled, extracted with ether which is then washed with water, dilute sodium hydroxide and water, dried over sodium sulfate and evaporated in vacuo. The residue is dissolved in 35 ml. of boiling ethanol to which is added gradually 13 g. of potassium hydroxide. The reaction is refluxed an additional hour and then evaporated to dryness in vacuo. The residue is dissolved in water and extracted with ether. The alkaline phase is acidified with 6 N sulfuric acid and extracted with ether. The ether is washed with water, dried over sodium sulfate and evaporated to dryness to obtain 3-mercapto-4-cyclohexylphenylglyoxylic acid.

The ethyl ester of the product is formed by reaction with absolute ethanol containing a small amount of anhydrous hydrochloric acid.

When ethyl 3-amino-4-cyclohexylphenylglyoxylate in the above example is replaced by equimolar amounts of the compounds of Example 8, then the corresponding products are prepared.

EXAMPLE 18

Ethyl 3-methylthio-4-cyclohexylphenylglyoxylate

To 3.85 g. of ethyl 3-mercapto-4-cyclohexylphenylglyoxylate in 40 ml. of water containing 0.65 g. of sodium hydroxide is added 2 ml. of dimethyl sulfate with stirring. The reaction mixture is gradually warmed to 40° C. and stirred for 2 hours. The mixture is cooled and extracted with ether which is washed with water, dried and evaporated in vacuo. The residue is distilled to obtain ethyl 3-methylthio-4-cyclohexylpherylglyoxylate.

When the above 3-methylthio-4-cyclohexylphenylglyoxylate is treated with 30% $H_2O_2$, then the resultant product is ethyl 3-methylsulfinyl-4-cyclohexylphenylglyoxylate or ethyl 3-methylsulfonyl-4-cyclohexylphenylglyoxylate.

When 3-mercapto-4-cyclohexylphenylglyoxylate in the above example is replaced by the compounds of Example 17, then the corresponding products are prepared.

When an equimolar amount of acetyl chloride is used in place of dimethyl sulfate in the above reaction, then the product prepared is ethyl 3-acetylthio-4-cyclohexylphenylglyoxylate.

EXAMPLE 19

Ethyl 3-chloro-5-trifluoromethyl-4-cyclohexylphenylglyoxylate

To a solution of 0.01 moles of ethyl 3-bromo-5-chloro-4-cyclohexylphenylglyoxylate in 50 ml. of dimethylformamide is added 0.15 moles of trifluoromethyl iodide and 0.02 g. of copper powder. The reaction is shaken in a sealed tube for 5 hours at 140° C., cooled, filtered and evaporated in vacuo. 200 ml. of water is added to the residue and extracted with ether. The ether extract is dried, evaporated to dryness and distilled to obtain ethyl 3-chloro-5-trifluoromethyl-4-cyclohexylphenylglyoxylate.

EXAMPLE 20

Ethyl 3-amino-5-chloro-4-cyclohexylphenylglyoxylate

A mixture of 17.6 g. (0.05 moles) of ethyl 3-chloro-5-nitro-4-cyclohexylphenylglyoxylate in 100 ml. of methanol containing 0.05 moles of citric acid and 1.5 g. of 5% palladium-on-carbon is shaken with hydrogen at 3 atm. pressure and 27° C. until 3 moles of hydrogen are absorbed. The mixture is filtered, washed with methanol and the filtrate concentrated in vacuo to obtain ethyl 3-amino-5-chloro-4-cyclohexylphenylglyoxylate isolated as the citrate salt.

EXAMPLE 21

1-(3-Chloro-4-cyclohexylphenyl)-1,2-ethanediol

To lithium aluminum hydride solution (3.9 M; 120 ml) diluted with anhydrous ether (750 ml) is added dropwise 150 g of ethyl 3-chloro-4-cyclohexylphenylglyoxylate with stirring, under nitrogen. The mixture is diluted with 250 ml of ether, and is stirred for 2 hours. The reaction mixture is acidified with 10% hydrochloric acid (450 ml) and extracted with ether/tetrahydrofuran. The aqueous fraction is washed three times with 50 ml portions of ether. The combined ether fractions are washed with water until neutral to litmus, and is dried over potassium carbonate. The ether is removed and the residue is triturated with n-hexane, filtered and air-dried to give 1-(3-chloro-4-cyclohexylphenyl)-1,2-ethanediol.

When ethyl 3-chloro-4-cyclohexylphenylglyoxylate in the above example is replaced by the appropriate glyoxylate of Examples 1-20, then the corresponding product is obtained.

EXAMPLE 22

1-Nitro-4-cyclohexylbenzaldehyde

A mixture of 0.66 moles of 3-nitro-4-cyclohexylphenylglyoxylate is stirred in 1.5 l. of boiling 10% sodium carbonate solution for 16 hours. The mixture is slowly filtered through charcoal into 1.1 l. of ice-cold 3 N-hydrochloric acid. The precipitate of crude material is collected on a filter, and recrystallized from benzene to give 3-nitro-4-cyclohexylphenylglyoxylic acid.

A mixture of 0.37 moles of 3-nitro-4-cyclohexylphenylglyoxylic acid is stirred under nitrogen in 250 ml. of boiling N,N-dimethylaniline for 16 hours. The cooled reaction mixture is poured into 700 ml. of ice-cold 3 N-hydrochloric acid and the crude product extracted into hexane. The product is purified by distillation under vacuum to obtain 1-nitro-4-cyclohexylbenzaldehyde.

When ethyl 3-nitro-4-cyclohexylphenylglyoxylate in the above example is replaced by the appropriate glyoxylates of Examples 1-20, then the corresponding product is obtained.

EXAMPLE 23

3-Chloro-4-cyclohexylbenzaldehyde

To 115 g. of 1-(3-chloro-4-cyclohexylphenyl)-1,2-ethanediol in tetrahydrofuran (800 ml.) is added a solution of periodic acid (102 g.) in ether (750 ml.). The reaction mixture is stirred under nitrogen overnight. The reaction mixture is filtered and the filtrate is washed with water (3×200 ml) and placed over sodium sulfate. Removal of solvent gives a liquid residue which is then distilled to give 3-chloro-4-cyclohexylbenzaldehyde.

When 1-(3-chloro-4-cyclohexylphenyl)-1,2-ethanediol in the above example is replaced by the diols of Example 21, then the corresponding aldehyde is prepared.

EXAMPLE 24

3-Chloro-4-cyclohexylcinnamic Acid

3-Chloro-4-cyclohexylbenzaldehyde (0.1 mole), malonic acid (0.2 moles), and dry pyridine (175 ml) are placed in a 1 l round-bottom flask. The malonic acid is dissolved by shaking on a steam bath and piperidine (0.5 ml) is added. The reaction is allowed to take place on the steam bath for 4 hours. After standing at room temperature overnight, the mixture is refluxed for 1 hour and cooled. The reaction mixture is poured into 250 ml of ice water and acidified with concentrated hydrochloric acid (80 ml) with stirring. The crystals of product are collected by filtration, washed with water (4×150 ml) and air dreid. Recrystallization from acetone-water gives 3-chloro-4-cyclohexylcinnamic acid.

When 3-chloro-4-cyclohexylbenzaldehyde in the above example is replaced by the aldehydes of Example 23, then the corresponding cinnamic acid is prepared.

EXAMPLE 25

Ethyl-3-chloro-4-cyclohexylcinnamate

3-Chloro-4-cyclohexylcinnamic acid (20.0 g.; 0.075 moles) is allowed to reflux with 8-10 pieces of Orierite in absolute ethanol (20 ml) containing concentrated sulfuric acid (5 ml) for 21 hours. The cooled reaction mixture is diluted with chloroform and filtered hot. The filtrate is washed 3 times with water, once with 10% sodium bicarbonate and twice more with water. After drying over sodium sulfate, the solvent is removed to give ethyl 3-chloro-4-cyclohexylcinnamate.

When 3-chloro-4-cyclohexylcinnamic acid in the above example is replaced by the cinnamic acids of Example 24, then the corresponding cinnamate is prepared.

EXAMPLE 26

Ethyl α,β-Dibromo-β-(3-chloro-4-cyclohexylphenyl)propionate

A cold solution of ethyl 3-chloro-4-cyclohexylcinnamate (0.075 moles) in chloroform (47 ml) is brominated by the portion-wise addition of bromine (4.1 ml; 10% excess) in chloroform (10 ml) with shaking and stirring. The solution is allowed to stand at room temperature for 1¼ hours and the solvent is removed to give ethyl α,β-dibromo-β-(3-chloro-4-cyclohexylphenyl)propionate.

When ethyl 3-chloro-4-cyclohexylcinnamate in the above example is replaced by the cinnamates of Example 25, then the corresponding α,β-dibromopropionate is prepared.

EXAMPLE 27

3-Chloro-4-cyclohexylpropiolic Acid

Powdered ethyl α,β-dibromo-β-(3-chloro-4-cyclohexyl)propionate (33.0 g.) is added portion-wise to 20% ethanolic potassium hydroxide (135 ml) at room temperature. The mixture is refluxed on a steam bath for 6 hours. The alcohol is evaporated and the residue is dissolved in water and covered with ether and is acidified with cold, dilute hydrochloric acid. The ether layer is washed with water, saline, and dried over sodium sulfate. The ether is removed to give a residue which is triturated with carbon tetrachloride. Recrystallization is carried out from acetic acid-water. This material is digested and triturated with boiling carbon tetrachloride to give 3-chloro-4-cyclohexylpropiolic acid.

When α,β-dibromo-β-(3-chloro-4-cyclohexyl)propionate in the above example is replaced by the α,β-dibromopropionate of Examle 26, then the corresponding propiolic acid is prepared.

EXAMPLE 28

3-Chloro-4-cyclohexylethynylbenzene 3-chloro-4-cyclohexylphenylpropiolic acid (7.3 g.) is heated at 120°-124° for 5 hours in quinoline. The reaction product is diluted with water and washed thoroughly with dilute hydrochloric acid. This is followed by washing with sodium bicarbonate (10%). The material is passed through a short aluminum (H+) column, eluted with N-hexane to give a fraction free of carbonyl absorption (I.R.). Removal of solvent gives 3-chloro-4-cyclohexylethynylbenzene.

When 3-chloro-4-cyclohexylphenylpropiolic acid in the above example is replaced by the propiolic acids of Example 27, then the corresponding acetylene is prepared.

EXAMPLE 29

3-Chloro-4-cyclohexylethynylbenzene

3-Chloro-4-cyclohexylacetophenone (0.25 moles) and phosphorus pentachloride (0.31 moles) are placed in a 3-necked flask equipped with a mechanical stirrer, a condenser connected to a nitrogen inlet, and a thermometer. The mixture is stirred at 33°-35° C. for 3 days. The cooled reaction mixture is poured onto 800 g. of ice and extracted with 3×500 ml. of ether. The ether fraction is washed with 2×100 ml water 4×100 ml of 5% sodium hydroxide, 3×50 ml water, 2×50 ml of saturated saline and dried over sodium sulfate. The ether is removed to give the chlorinated intermediate. The intermediate is dissolved in anhydrous THF (200 ml) and is added dropwise to a freshly prepared solution of sodamide in liquid ammonia, using a dry-ice condenser. The reaction mixture is allowed to stir at room temperature overnight; then, it is poured into 50 ml of water and 500 ml of ether. The ether fraction is washed with 3×50 ml water and 50 ml of saturated saline and is dried over sodium sulfate. Removal of solvent gives a residue which is distilled to give 3-chloro-4-cyclohexylethynylbenzene.

EXAMPLE 30

When the procedures of Examples 1–29 are followed, the compounds below may be prepared.
p-cyclopentylethynylbenzene
p-cyclohexylethynylbenzene
p-cycloheptylethynylbenzene
3-bromo-4-cyclohexylethynylbenzene
3-fluoro-4-cyclohexylethynylbenzene
3-iodo-4-cyclohexylethynylbenzene
3-nitro-4-cyclohexylethynylbenzene
3-trifluoromethyl-4-cyclohexylethynylbenzene
3-amino-4-cyclohexylethynylbenzene
3-methylamino-4-cyclohexylethynylbenzene
3-acetylamino-4-cyclohexylethynylbenzene
3-dimethylamino-4-cyclohexylethynylbenzene
3-cyano-4-cyclohexylethynylbenzene
3-hydroxy-4-cyclohexylethynylbenzene
3-methoxy-4-cyclohexylethynylbenzene
3-acetyloxy-4-cyclohexylethynylbenzene
3-mercapto-4-cyclohexylethynylbenzene
3-methylthio-4-cyclohexylethynylbenzene
3-methylsulfinyl-4-cyclohexylethynylbenzene
3-methylsulfonyl-4-cyclohexylethynylbenzene
3-acetylthio-4-cyclohexylethynylbenzene
3,5-dichloro-4-cyclohexylethynylbenzene
3-chloro-5-trifluoromethyl-4-cyclohexylethynylbenzene
3,5-dinitro-4-cyclohexylethynylbenzene
3-chloro-5-nitro-4-cyclohexylethynylbenzene
3-chloro-5-amino-4-cyclohexylethynylbenzene
3-chloro-5-bromo-4-cyclohexylethynylbenzene
3-chloro-5-fluoro-4-cyclohexylethynylbenzene
3-chloro-4-cyclopentylethynylbenzene
3-bromo-4-cyclopentylethynylbenzene
3-fluoro-4-cyclopentylethynylbenzene
3-trifluoromethyl-4-cyclopentylethynylbenzene
3-nitro-4-cyclopentylethynylbenzene
3-cyano-4-cyclopentylethynylbenzene
3-methylsulfonyl-4-cyclopentylethynylbenzene
3,5-dichloro-4-cyclopentylethynylbenzene
3-chloro-5-nitro-4-cyclopentylethynylbenzene
3-chloro-4-cycloheptylethynylbenzene
3-bromo-4-cycloheptylethynylbenzene
3-fluoro-4-cycloheptylethynylbenzene
3-trifluoromethyl-4-cycloheptylethynylbenzene
3-nitro-4-cycloheptylethynylbenzene
3-cyano-4-cycloheptylethynylbenzene
3-methylsulfonyl-4-cycloheptylethynylbenzene
3,5-dichloro-4-cycloheptylethynylbenzene
3-chloro-5-nitro-4-cycloheptylethynylbenzene
p-isopropylethynylbenzene
p-isobutylethynylbenzene
3-chloro-4-methylethynylbenzene
3-chloro-4-ethylethynylbenzene
3-chloro-4-propylethynylbenzene
3-chloro-4-i-propylethynylbenzene
3-chloro-4-butylethynylbenzene
3-chloro-4-i-butylethynylbenzene
3-chloro-4-sec-butylethynylbenzene
3-chloro-4-t-butylethynylbenzene
3-chloro-4-pentylethynylbenzene
3-chloro-4-hexylethynylbenzene
3-chloro-4-heptylethynylbenzene
3-nitro-4-i-propylethynylbenzene
3-nitro-4-i-butylethynylbenzene
3-bromo-4-i-butylethynylbenzene
3-fluoro-4-i-butylethynylbenzene 3-cyano-4-i-butylethynylbenzene
3-methylsulfonyl-4-i-butylethynylbenzene
3-trifluoromethyl-4-i-butylethynylbenzene
2'-chloro-4-ethynylbiphenyl
2'-fluoro-4-ethynylbiphenyl
2'-bromo-4-ethynylbiphenyl
2'-nitro-4-ethynylbiphenyl

I claim:

1. A method of treating inflammation, pain or fever in a warm-blooded animal which comprises administering to the animal an effective amount of an active compound of the formula:

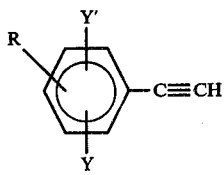

where
R is hydrogen, alkyl of 1 to 7 carbon atoms, cycloalkyl of 4 to 7 carbon atoms, 1 to 7 carbon atoms alkyl substituted cycloalkyl of 5 to 7 carbon atoms, cycloalkenyl of 5 to 7 carbon atoms, phenyl or substituted phenyl where the substituent is Y''',
Y and Y' are each selected from the group consisting of hydrogen and hydroxy
Y'' is selected from the group consisting of Y, lower alkyl, and trifluoromethyl,
with the proviso that at least one of Y and Y' is other than hydrogen.

2. The method of claim 1, wherein the active compound is of the formula

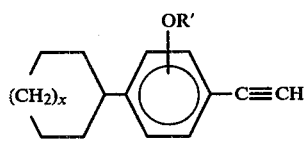

where x is 0–2, and R' is hydrogen.

3. The method of claim 1, wherein the active compound is 3-hydroxy-4-cyclohexylethynylbenzene.

4. A method of treating inflammation, pain or fever in a warm-blooded animal which comprises administering to the animal an effective amount of an active compound of the formula:

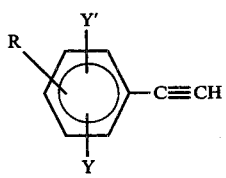

where
R is hydrogen, alkyl of 1 to 7 carbon atoms, cycloalkyl of 4 to 7 carbon atoms, 1 to 7 carbon atoms alkyl substituted cycloalkyl of 5 to 7 carbon atoms, phenyl or substituted phenyl where the substituent is Y''',
Y, Y' and Y'' are each selected from the group consisting of hydrogen and hydroxy, and with the proviso that at least one of Y, Y' and Y'' is other than hydrogen.

5. The method of claim 4, wherein the active compound is of the formula

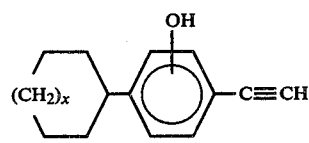

where x is 0–2.

6. A pharmaceutical preparation in a dosage unit form adapted for administration to warm-blooded animals for the treatment of inflammation, pain or fever, comprising an effective amount of an active compound of the formula

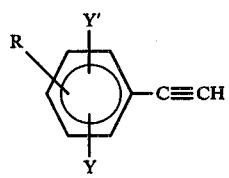

where
R is hydrogen, alkyl of 1 to 7 carbon atoms, cycloalkyl of 5 to 7 carbon atoms, 1 to 7 carbon atoms alkyl substituted cycloalkyl of 5 to 7 carbon atoms, cycloalkenyl of 5 to 7 carbon atoms, phenyl or substituted phenyl where the substituent is Y''';
Y and Y' are each selected from the group consisting of hydrogen and hydroxy;
Y'' is selected from the group consisting of Y, lower alkyl, and trifluoromethyl,
with the proviso that at least one of Y and Y' is other than hydrogen.

7. The preparation of claim 6, wherein the active compound is of the formula

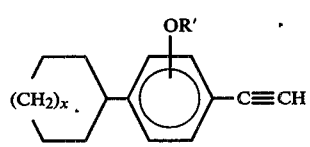

wherein x is 0–2, and R' is hydrogen.

8. The preparation of claim 7, wherein the active compound is 3-hydroxy-4-cyclohexylethynylbenzene.

9. A pharmaceutical preparation in a dosage unit form adapted for administration to warm-blooded animals for the treatment of inflammation, pain or fever, comprising an effective amount of an active compound of the formula

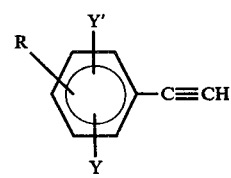

where
R is hydrogen, alkyl of 1 to 7 carbon atoms, cycloalkyl of 5 to 7 carbon atoms, 1 to 7 carbon atoms alkyl substituted cycloalkyl of 5 to 7 carbon atoms, cycloalkenyl of 5 to 7 carbon atoms, phenyl or substituted phenyl where the substituent is Y';

Y, Y' and Y" are each selected from the group consisting of hydrogen and hydroxy, with the proviso that at least one of Y, Y' and Y", is other than hydrogen, and a suitable pharmaceutically acceptable carrier.

10. The preparation of claim 9 wherein the active compound is of the formula

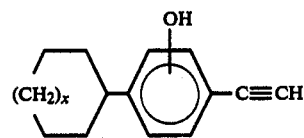

wherein x is 0–2.

UNITED STATES PATENT AND TRADEMARK OFFICE
CERTIFICATE OF CORRECTION

PATENT NO. : 4,166,133
DATED : August 28, 1979
INVENTOR(S) : Julius Diamond

It is certified that error appears in the above-identified patent and that said Letters Patent are hereby corrected as shown below:

Column 2, line 15, change "Y' " to---Y"---

Column 14, line 53, change "3-methylthio-4-cyclohexylpheryl-glyoxy-" to--3-methylthio-4-cyclohexyl-phenylglyoxy- ---

Column 16, line 35, change "dreid" to--dried--

Column 17, line 55, after "water" insert--,--

Signed and Sealed this

First Day of January 1980

[SEAL]

Attest:

Attesting Officer

SIDNEY A. DIAMOND

Commissioner of Patents and Trademarks